United States Patent
Cioca et al.

(10) Patent No.: US 6,231,874 B1
(45) Date of Patent: May 15, 2001

(54) STRUCTURED WATER FOR ENHANCED MOISTURIZATION

(75) Inventors: Gheorghe Cioca, Lake Grove; Andrew J. Bevacqua, E. Setauket; Joseph Gubernick, New York; Nicolae Vrabie, Jackson Heights, all of NY (US)

(73) Assignee: Color Access, Inc., Melville, NY (US)

( * ) Notice: Subject to any disclaimer, the term of this patent is extended or adjusted under 35 U.S.C. 154(b) by 0 days.

(21) Appl. No.: 09/042,345

(22) Filed: Mar. 13, 1998

(51) Int. Cl.⁷ .............................. A61K 6/00; A61K 7/035
(52) U.S. Cl. ......................... 424/401; 424/69; 514/937; 514/938
(58) Field of Search ................... 424/401, 78.03, 424/69; 514/937, 938

(56) References Cited

FOREIGN PATENT DOCUMENTS

| | | |
|---|---|---|
| 0826636 A1 | 3/1998 | (EP) . |
| 62-258312 * | 11/1987 | (JP) . |
| 1-258611 | 10/1989 | (JP) . |
| 7096282 | 4/1995 | (JP) . |
| 7185550 | 7/1995 | (JP) . |
| 7265860 | 10/1995 | (JP) . |
| 7277994 | 10/1995 | (JP) . |
| 7277996 | 10/1995 | (JP) . |
| 88053 | 7/1984 | (RO) . |
| 88054 | 7/1984 | (RO) . |
| 107544 B1 | 3/1996 | (RO) . |
| 107545 B1 | 3/1996 | (RO) . |
| 107546 B1 | 3/1996 | (RO) . |
| 109835 B1 | 3/1996 | (RO) . |
| WO 90/15779 | 12/1990 | (WO) . |
| 9606048 A1 | 2/1996 | (WO) . |

OTHER PUBLICATIONS

Structured Water: Its Healing Effects On The Diseased State, Mikesell, Norman D., published, 1985, Retrieved from the internet on Sep. 9, 1999; http://www.naturesalternatives.com/lc/mikesell.html; p. 1, first paragraph and p. 6, lines 16–20.

Stillinger, Water Revisited, Science, vol. 209, No. 4455, Jul. 25, 1980, pp. 451–457.

Christof et al., Optimization of Culture Media in the Presence of Active Water in Order to Obtain Amylolytic Enzyme of Fungic Nature, Roum. Biotechnol. Lett., 3(6), 53–58, 1998.*

* cited by examiner

Primary Examiner—Thurman K. Page
Assistant Examiner—Brian K. Seidleck
(74) Attorney, Agent, or Firm—Kenyon & Kenyon

(57) ABSTRACT

The invention relates to a cosmetic or pharmaceutical composition containing a moisturizing effective amount of S water, as well as a method for enhancing the moisturization capacity of a skin care composition containing an aqueous component comprising incorporating S water as all or part of the aqueous component

14 Claims, No Drawings

STRUCTURED WATER FOR ENHANCED MOISTURIZATION

FIELD OF THE INVENTION

The present invention relates to aqueous cosmetic compositions. In particular, the invention relates to cosmetic compositions which have improved properties by virtue of the use of structured water.

BACKGROUND OF THE INVENTION

Water is the predominant component of the human body, and in fact of all living things. It is an essential participant in metabolic and synthetic processes in the body. There has been much speculation on how water interacts with cellular components, and many authors have speculated that water may in fact change structure and function once it has been taken into tissues and cells(see, e.g., Benal and Fowler, Trends Biochem. Sci. 8: 1, 1983; Stillinger, Science 209: 4455, 1980; Frank and Wen, Proc. R. Soc. Lond., 1980: A247, 1981; Franks, Water, A Comprehensive Treatise, London, 1981).

In connection with the possible alteration of water's structure, it has been shown (Bernal and Fowler, supra) that an equilibrium exists in water between the $(H_3O)^+$ and $(OH)^-$ structures, in the absence of an ordering electric field. It has been more recently shown (RO 88053/1987; RO 88054/1987; and RO 109835/1995) that if a polarizing electrical field is passed through the water, the equilibrium is destroyed, and the two component ions begin to move independently. Therefore, the generation of this electric field between two electrodes results in a "structuring" process in water, wherein the $R^-H^+_n$ structures, in which $R^-$ represents a polymeric radical, migrates in the direction of the positive electrode, accumulating as "acid water"; similarly, the $R'(OH)^-_n$ components migrate toward the negative electrode, giving rise to "basic water". Many phenomena may contribute to the structuring of water, and aqueous solutions, including alignment of the dipole moments of water molecules, transport of existing charges in solutions toward the electrodes, magnitude of the applied potential difference, influence of the nature, size and shape of the electrode surface, and $H^+$ and $OH^-$ tunneling. Whatever the influences resulting in structuring, however, the structured (or "activated") water is defined as water that contains stabilized clusters of ions. The acid fraction is alternately referred to as structured water I for "I water") containing stabilized clusters of $R^+(H)^-(Cl^-, PO_4^{3-}, SO_4^{2-})$ ions. The basic fraction is alternately referred to as structured water S (or "S water") which contains stabilized clusters of $R+(OH)-n$ ($Ca^{2+}$, $Mg^{2+}$, $Na^+$, $K^+$, etc.) ions. To further distinguish the two types of water, I water is characterized by a conductivity $C(\mu S/cm)$ of about 900–2500 and pH of about 1.9–2.5; S water is characterized by a conductivity $C(\mu S/cm)$ of about 400–1500, and a pH of about 10.5–12, each resulting from tap water with $C(\mu S/cm)$ of about 330, and a pH of about 7.4.

Substantial differences are found among the UV spectra of I, S. tap and deionized water, particularly in the 200–250 nm band. When their reactivities are measured in an electronographic field, I, S and tap waters also show significant differences. In particular, for tap water, the total light flux after electronographic stimulation has a positive impulse $I^+$ substantially equivalent to it negative impulse $I^-$. For structured water, the S water stimulated in the same way in positive impulse shows a very high light reactivity, whereas the negative impulse reactivity is almost equivalent to that of distilled water, yielding a positive to negative ratio of greater than 1; in contrast, the reactivity of the I water samples shows a high negative impulse, with a positive impulse approximately equivalent to distilled water, the ratio of positive to negative being less than 1. Different biological properties have been suggested for each type of water. These demonstrated differences in structure between the two types of structured waters have been said to correlate with their biological activities: S water is said to have a stimulatory effect on enzymatic and other biosynthetic processes, whereas I water is said to be inhibitory of the same processes.

Structured water has been disclosed for use in cosmetic compositions previously, in, for example RU 107544, RU 107545 and RU 107546, which relate to the use of I water in specific cosmetic products, for the treatment of oily skin, dry skin, or acne. However, a specific biological effect has not been attributed directly to I water in such compositions, and no information has been provided on possible utility of S water in cosmetic compositions. It has now been discovered that the use of S water can have beneficial effects on the moisturizing capacity of compositions for topical application to the skin.

SUMMARY OF THE INVENTION

The invention relates to topically applied skin-care compositions containing a moisturizing-effective amount of S water. The invention also relates to a method for increasing the moisturizing capacity of a skin care composition containing an aqueous component, the method comprising incorporating S water as all or part of the aqueous component. The invention also provides a method of moisturizing the skin comprising applying to the skin a moisturizing effective amount of S water

DETAILED DESCRIPTION OF THE INVENTION

As noted above, structured water and methods for making same are well known in the art. For example, RO 88053 describes a method for producing "B" or basic (S-type) water, and RO 88054 discloses a method for making "A" or acid (I-type) water. Improvements in making either of these types of water are further described in Wo 9606048. The contents of each of these documents is incorporated herein by reference.

It has now been unexpectedly discovered that S water has a greater moisturization capacity than ordinary water or structured I water. In particular, it has been observed that skin treated with a composition containing S water provides a measurable, significantly increased skin surface water content, when compared with the results observed with other waters. Thus, S water is a particularly useful component in cosmetic and pharmaceutical compositions in which moisturizing properties are desired.

The S water can be used alone as a moisturizer, for example as a moisturizing spray or rub-on composition. More often, however, S water will be used a part of a more complex composition, for example as part of a hydroalcoholic product, or as part of a water-in-oil or oil-in-water emulsion. The S water can be used in the composition within the range of from about 1 to about 100% by weight, but generally will be in the range of from about 20 to about 80%, more preferably from about 40 to about 80%, particularly when used as part of an oil/water emulsion. The form the vehicle takes can be any which is suitable for topical application to the skin, for example, solutions, colloidal dispersions, emulsions, suspensions, creams, lotions, gels, foams, mousses, sprays and the like.

S water can be used in virtually any type of skin care product which has an aqueous component. For example, it can be used to confer moisturizing properties to makeup products, such as lipsticks and glosses, foundations, blushes, eyeliners, eyeshadows and the like. It will also be useful in treatment products, including pharmaceutical products, in which moisturizing properties are desired to complement the activity of the principle active, or necessary to offset the drying properties of an otherwise beneficial active. It is particularly contemplated that S water be combined with other moisturizing components, such as emollients, humectants and occlusive agents. Agents of this type are described in the International Cosmetic Ingredients Handbook, Third Edition, 1996, the contents of which are incorporated herein by reference. In addition, however, it can also be beneficial in combination with non-moisturizing topically applied actives, for example, analgesics, anesthetics, anti-acne agents, antibacterials, antiyeast agents, antifungal agents, antioxidants, antiviral agents, antidandruff agents, antidermatitis agents, antipruritic agents, antiemetics, antimotion sickness agents, anti-irritant agents, anti-inflammatory agents, antihyperkeratolytic agents, anti-dry skin agents, antiperspirants, antipsoriatic agents, antiseborrheic agents, hair conditioners and hair treatment agents, antiaging agents, antiwrinkle agents, sunscreen agents, antihistamine agents, skin lightening agents, depigmenting agents, wound-healing agents, vitamins, corticosteroids, tanning agents, or hormones.

The cosmetic compositions of the invention can be applied on an as-needed basis, for example, when makeup is normally applied, or applied to the skin when the skin is feeling dry, or during or after exposure to drying conditions, such as cold or wind. However, the moisturization achieved is temporary, lasting a period of several hours; therefore, a preferred method of obtaining the benefits of the composition is via chronic topical application of the S-water containing composition. It is suggested as an example that topical application of the composition, in an amount of from about 0.1 $\mu$g/cm$^2$ to 5 mg/cm$^2$ of exposed skin, be performed from about once per week to about 4 or 5 times daily, preferably from about 3 times a week to about 3 times daily, most preferably about once or twice per day. By "chronic" application, it is meant herein that the period of topical application may be over the lifetime of the user, preferably for a period of at least about one month, more preferably from about three months to about twenty years, more preferably from about six months to about ten years, more preferably still f about one year to about five years. It will of course be recognized that the mode of application of S water in combination with therapeutic actives will be governed by the recommended regimen for the active.

The invention is further illustrated by the following non-limiting examples.

EXAMPLES

Example I

Three compositions are prepared for testing. Each is an oil-in-water emulsion, containing about 60% water, and no active components. One emulsion is prepared with non-structured, deionized (DI) water, one with structured I water, and the third with S water, as the aqueous component. Fifteen female panelists are chosen for participation. The test sites are the right and left facial cheeks. The women are instructed to refrain from using any treatment products on the test sites the day of testing. On the morning of testing, the subjects are instructed to wash their faces at least one hour before testing begins, and equilibrated in the environmental room at 40% relative humidity and 70° F. for 20 minutes. One test product is applied at 2mg/cm$^2$ to the right cheek, and another applied to the left facial cheek. The panelists are instructed not to wash the test sites for the duration of the study.

Skin evaluations are carried out before treatment (baseline), 5 minutes, 30 minutes, 1, 2, 4 and 6 hours after product application. Skin moisturization is measured on the right and left facial cheeks before and after product use via the Nova DPM 9003. The Nova measures skin moisturization as a function of increased skin surface water content, in which the output is proportional to the skin's electrical capacitance in the Mhz. frequency range. Data acquisition is software controlled. The difference in electrical capacitance before and after treatment is calculated. The higher the skin water content, the higher the electrical capacitance, and hence, the more moisturized the skin. The results are shown in Table 1.

TABLE 1

| Time | with DI water | with I water | with S water | DI vs. I | DI vs. S | I vs. S |
|---|---|---|---|---|---|---|
| 5 min. | 45% | 44% | 63% | NS | p < 05 | p < 05 |
| 30 min. | 35% | 37% | 49% | NS | p < 05 | p < 05 |
| 1 hour | 22% | 27% | 40% | NS | p < 05 | p < 05 |
| 2 hours | 18% | 23% | 31% | NS | p < 05 | p < 05 |
| 4 hours | 17% | 19% | 28% | NS | p < 05 | p < 05 |
| 6 hours | 14% | 15% | 23% | NS | p < 05 | p < 05 |

All products increased moisturization significantly over baseline, indicating some effect of the vehicle in moisturization. However, the results show that the increase in moisturization achieved by S water is significantly greater than that achieved by either the DI-containing product or the I water-containing product, over a six hour period of time, whereas there is no statistical difference between moisturization achieved by DI- and I water-containing products.

What is claimed is:

1. A topical cosmetic or pharmaceutical composition containing a moisturizing effective amount of S water, combined with at least one other cosmetic or pharmaceutical component, wherein the S water is characterized by a conductivity of about 400–1500 and a pH of about 10.5–12, resulting from tap water with a conductivity of about 330 and a pH of about 7.4.

2. The composition of claim 1 in which S water is present in an amount of from about 1% to about 100%.

3. The composition of claim 1 in which S water is present in an amount of from about 20% to about 80%.

4. The composition of claim 1 which is a hydroalcoholic composition, a water-in-oil emulsion, or an oil-in-water emulsion.

5. The composition of claim 1 which further comprises at least one additional moisturizing agent.

6. The composition of claim 1 which further comprises at least one biologically active agent.

7. The composition of claim 1 which is a makeup product.

8. The composition of claim 1 which is a skin treatment product.

9. A method for increasing the moisturizing capacity of a skin care composition containing an aqueous component comprising incorporating S water as all or part of the aqueous component, the water combined with at least one other cosmetic or pharmaceutical component, wherein the S water is characterized by a conductivity of about 400–1500 and a pH of about 10.5–12, resulting from tap water with a conductivity of about 330 and a pH of about 7.4.

10. The method of claim 9 in which S water comprises from about 20 to about 80% of the composition.

11. The method of claim 9 in which S water is combined with at least one other moisturizing agent.

12. A method of moisturizing the skin comprising applying to the skin a moisturizing effective amount of S water, combined with at least one other cosmetic or pharmaceutical component, wherein the S water is characterized by a conductivity of about 400–1500 and a pH of about 10.5–12, resulting from tap water with a conductivity of about 330 and a pH of about 7.4.

13. The method of claim 12 in which S water is applied with at least one additional moisturizing agent.

14. The method of claim 12 in which S water is applied with at least one biologically active agent.

* * * * *